(12) United States Patent
Ham

(10) Patent No.: US 10,750,948 B2
(45) Date of Patent: Aug. 25, 2020

(54) ULTRASLOW LIGHT AND NONDEGENERATE PHASE CONJUGATION-BASED REAL-TIME, NON-INVASIVE, IN-VIVO DEEP-TISSUE OPTICAL IMAGING APPARATUS, PHOTODYNAMIC THERAPY APPARATUS, OPTICAL IMAGING METHOD AND PHOTODYNAMIC THERAPY METHOD

(71) Applicant: GWANGJU INSTITUTE OF SCIENCE AND TECHNOLOGY, Gwangju (KR)

(72) Inventor: Byoung Seung Ham, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 709 days.

(21) Appl. No.: 15/247,919

(22) Filed: Aug. 26, 2016

(65) Prior Publication Data

US 2017/0055838 A1    Mar. 2, 2017

(30) Foreign Application Priority Data

Aug. 26, 2015  (KR) ................. 10-2015-0120041

(51) Int. Cl.
| | |
|---|---|
| *A61B 5/05* | (2006.01) |
| *A61B 5/00* | (2006.01) |
| *A61N 5/06* | (2006.01) |
| *G01N 21/63* | (2006.01) |
| *G01N 21/47* | (2006.01) |
| *G02F 1/35* | (2006.01) |

(52) U.S. Cl.
CPC .......... *A61B 5/0073* (2013.01); *A61B 5/0097* (2013.01); *A61N 5/062* (2013.01); *G01N 21/4795* (2013.01); *G01N 21/636* (2013.01); *G02F 1/3538* (2013.01)

(58) Field of Classification Search
CPC ................................ G02F 1/33; G02F 1/3538
See application file for complete search history.

(56) References Cited

U.S. PATENT DOCUMENTS

| | | | |
|---|---|---|---|
| 7,020,372 B2* | 3/2006 | Lee ........................ | B82Y 10/00 257/E21.09 |
| 2014/0009808 A1* | 1/2014 | Wang ........................ | G02F 1/33 359/10 |

OTHER PUBLICATIONS

Daniel S. Elson et al., "Ultrasound-mediated optical tomography: a review of current methods", Interface Focus vol. 1, p. 632 (2011), 17 pages.
Paul Beard, "Biomedical photoacoustic imaging", Interface Focus vol. 1, p. 602 (2011), 30 pages.
Aaron Fenster et al., "Three-dimensional ultrasound scanning", Interface Focus vol. 1, p. 503 (2011), 17 pages.
(Continued)

*Primary Examiner* — Michael J D Abreu
(74) *Attorney, Agent, or Firm* — Hauptman Ham, LLP

(57) ABSTRACT

The present invention provides a method which can significantly increase the signal-to-noise ratio of an ultrasound-modulated optical signal by overcoming the shallow depth problem of in vivo optical imaging in existing optical imaging by use of a quantum optical phenomenon based on ultraslow light and nondegenerate phase conjugation and which can be applied directly not only to medical optical imaging, but also to medical photodynamic therapy, through slow light amplification of phase conjugate waves.

10 Claims, 7 Drawing Sheets

(56) References Cited

OTHER PUBLICATIONS

J.P. Monchalin et al., "Broadband optical detection of ultrasound by optical sideband stripping with a confocal Fabry-Perot", Appl. Phys. Lett. vol. 55, p. 1612 (1989), 4 pages.

Guy Rousseau et al., "Ultrasound-modulated optical imaging using a high-power pulsed laser and a double-pass confocal Fabry-Perot interferometer", Optical Society of America, Opt. Lett. vol. 34, p. 3445 (2009), 3 pages.

Youzhi Li et al., "Pulsed ultrasound-modulated optical tomography using spectral-hole burning as a narrowband spectral filter", Appl. Phys. Lett., AIP Publishing, vol. 93, p. 011111 (2008), 4 pages.

Yan Liu et al., "Optical focusing deep inside dynamic scattering media with near-infrared time-reversed ultrasonically encoded (TRUE) light", Nature Communications vol. 6, Macmillan Publishers Limited, p. 5904 (2014), 9 pages.

Amit P. Jathoul et al., "Deep in vivo photoacoustic imaging of mammalian tissues using a tyrosinase-based genetic reporter", Nature Photon. vol. 9, Macmillan Publishers Limited, p. 243 (2015), 8 pages.

R. W. Boyd, "Nonliner Optics (3rd Edition)" (Academic Press, 1992) Ch. 6, 620 pages.

Lihong V. Wang et al., "Photoacoustic Tomography: In Vivo Imaging from Organelles to Organs", Science vol. 335, p. 1458 (2012), 6 pages.

Geng Ku et al., "Deeply penetrating photoacoustic tomography in biological tissues enhanced with an optical contrast agent", Opt. Lett. vol. 30, Optical Society of America, p. 507 (2005), 3 pages.

Stephen E. Harris, "Electromagnetically Induced Transparency", Physics Today vol. 50, No. 7, American Institute of Physics, p. 36 (1997), 7 pages.

T. Utikal et al., "Spectroscopic detection and state preparation of a single praseodymium ion in a crystal", Nature Communications vol. 5, 2014 Macmillan Publishers Limited, p. 3627 (2014), 8 pages.

Byoung S. Ham et al., "Transmission enhancement of ultraslow light in an atom shelved model of spectral hole burning solids", Opt. Exp. vol. 17, p. 9369 (2009), 7 pages.

Lene Vestergaard Hau et al., "Light speed reduction to 17 metres per second in an ultracold atomic gas", Nature vol. 397, 1999 Macmillan Magazines Ltd, p. 594 (1999), 5 pages.

A.V. Turukhin et al., "Observation of Ultraslow and Stored Light Pulses in a Solid", Phys. Rev. Lett. vol. 88, 2002 the American Physical Society, p. 023602 (2002), 4 pages.

B.S. Ham et al., "Efficient electromagnetically induced transparency in a rare-earth doped crystal", Opt. Communi. vol. 144, 1997 Elsevier Science B.V., p. 227 (1997), 4 pages.

B.S. Ham et al., "Enhanced nondegenerate four-wave mixing owing to electromagnetically induced transparency in a spectral hole-burning crystal", Opt. Lett. vol. 22, 1997 Optical Society of America, p. 1138 (1997), 3 pages.

B.S. Ham et al., "Efficient phase conjugation via two-photon coherence in an optically dense crystal", Phys. Rev. A vol. 59, 1999 the American Physical Society, p. R2583 (1999), 4 pages.

P.R. Hemmer et al., "Efficient low-intensity optical phase conjugation based on coherent population trapping in sodium", Opt. Lett. vol. 20, 1995 Optical Society of America, p. 982 (1995), 3 pages.

B.S. Ham et al., "Enhancement of four-wave mixing and line narrowing by use of quantum coherence in an optically dense double-$\Lambda$ solid", Opt. Lett. vol. 24, p. 86 (1999), 1999 Optical Society of America, 3 pages.

Danielle A. Braje et al., "Low-light-level nonlinear optics with slow light", Phys. Rev. A vol. 68, p. 041801(R) (2003), 2003 the American Physical Society, 4 pages.

Byoung S. Ham, "Enhancement of optical echoes by using ultraslow light", OSA NLO 2015 conference, W4A, Hawaii, USA (2015), 2 pages.

Michael M. Kash et al., "Ultraslow Group Velocity and Enhanced Nonlinear Optical Effects in a Coherently Driven Hot Atomic Gas", Phys. Rev. Leff. vol. 82, p. 5229 (1999), 1999 the American Physical Society, 4 pages.

S. E. Harris et al., "Nonlinear Optics at Low Light Levels", Rev. Lett. vol. 82, 1999 the American Physical Society p. 4611 (1999), 4 pages.

Dennis E.J.G.J. Dolmans et al., "Photodynamic therapy for cancer", Nature Reviews Cancer vol. 5, p. 380 (2003), 2003 Nature Publishing Group, 8 pages.

B.S. Ham et al., "Efficient phase conjugation via two-photon coherence in an optically dense crystal", Phys. Rev. A vol. 59, p. R2583 (1999), 1999 the American Physical Society, 4 pages.

* cited by examiner

ULTRASLOW LIGHT AND NONDEGENERATE PHASE CONJUGATION-BASED REAL-TIME, NON-INVASIVE, IN-VIVO DEEP-TISSUE OPTICAL IMAGING APPARATUS, PHOTODYNAMIC THERAPY APPARATUS, OPTICAL IMAGING METHOD AND PHOTODYNAMIC THERAPY METHOD

CROSS REFERENCE TO RELATED APPLICATION

This application claims the benefit of Korean Patent Application No. 10-2015-0120041, filed on Aug. 26, 2015, entitled "ULTRASLOW LIGHT AND NONDEGENERATE PHASE CONJUGATION-BASED REAL-TIME, IN-VIVO, DEEP-TISSUE OPTICAL IMAGING APPARATUS, A PHOTO DYNAMIC THERAPY APPARATUS, OPTICAL IMAGING METHOD AND PHOTO DYNAMIC THERAPY METHOD", which is hereby incorporated by reference in its entirety into this application.

BACKGROUND

1. Technical Field

The present invention relates to an optical imaging apparatus and method, and more particularly, to an ultraslow light and nondegenerate phase conjugation-based real-time, non-invasive, in vivo deep-tissue optical imaging apparatus and optical imaging method, which use a nonlinear medium having four energy levels and at least three optical pulses that resonate or near-resonate between the energy levels of the optical medium. Herein, the term "deep-tissue" means a tissue having a depth on the order of cm.

2. Related Art

In in vivo optical imaging, light scattering in a heterogeneous substance such as bio-tissue is the biggest problem that interferes with the application of optical tomography to the medical field by distorting optical images and significantly decreasing signal-to-noise ratios.

Optical coherence tomography (OCT; http://en.wikipedia.org/wiki/Optical coherence tomography; http://www.zeiss.com/) is the only examine in which optical imaging is applied to the eye's retina and cornea which require only images having a shallow bio-tissue depth of 1 mm or less. To overcome the problem of light scattering in bio-tissue, ultrasound has been applied to optical imaging techniques such as ultrasound-modulated optical tomography (UOT; Interface Focus Vol. 1, p. 632 (2011)) and photoacoustic tomography (PAT; Interface Focus Vol. 1, p. 602 (2011)). Herein, the ultrasound is the key to increase in vivo imaging depth (Interface Focus Vol. 1, p. 503 (2011)). The reason is because ultrasound is weakly absorbed by bio-tissue or weakly scattered in bio-tissue. Meanwhile, light generally shows good characteristics in the contrast of images. Thus, to maintain the in vivo deep-tissue imaging advantage of ultrasound and add good contrast of light, it is required to combine ultrasound with light waves. The resulting ultrasound-modulated light waves enhance both resolution and imaging depth in optical imaging. Herein, to distinguish the ultrasound-modulated optical signal from the background noises of other optical signals to thereby increase signal-to-noise ratios, a Fabry-Perot interference system (Appl. Phys. Lett. Vol. 55, p. 1612 (1989); Opt. Lett. Vol. 34, p. 3445 (2009)) or a spectral hole burning technique (Appl. Phys. Lett. Vol. 93, p. 011111 (2008)) have been applied.

In recent years, ultrasound-modulated optical tomography techniques have been intensively studied to apply degenerate optical phase conjugation at the same wavelength to optical imaging, and the phase conjugation is a nonlinear optical phenomenon having time-reversible properties, which accurately reverses the propagation direction of light waves (Nature Communications Vol. 6, p. 5904 (2014)). The phase conjugation has the property of accurately and perfectly removing image distortions caused by all phase variations generated in scattering media, and thus the imaging resolution can be increased to the ultrasonic wavelength limits.

In recent years, in order to apply phase conjugation to ultrasound-modulated optical tomography to thereby increase resolution and depth, a photorefractive material or a spatial light modulator (SLM) has been used. Furthermore, because scattered optical signals are very weak, optical phase conjugate waves can be artificially generated using a spatial light modulator, and the intensity thereof can also be increased (Nature Photon. Vol. 9, p. 243 (2015). Although the switching time of the spatial light modulator has been shortened owing to the development of electronic devices for the past ten years, a spatial light modulator-based ultrasound-modulated optical tomography technique has not yet been applied to real-time in vivo optical imaging due to the slow imaging time. More specifically, there is an inversely proportional relationship between the individual pixel size of the spatial light modulator, which determines the imaging resolution, and the pixel number which determines the total switching time. To make phase conjugate waves for each of ultrasound-modulated optical signals incident to each pixel of the spatial light modulator, the signals should be processed by a computer, and the processing time is limited by the frame rate of the spatial light modulator, and thus an SLM having 1,000,000 pixels does not reach even kHz (Hamamatsu LCOS-SLM). Thus, when a bio-tissue volume of 10 cm×10 cm×10 cm is scanned by ultrasound-modulated optical tomography with a resolution of 0.1 mm at a kHz rate, the total scan time is 10,000 seconds (about 166 minutes) or more. Namely, due to the temporal limit of the spatial light modulator, apart from imaging depth, even the latest ultrasound-modulated optical tomography technology cannot be applied to optical medical diagnosis.

Meanwhile, in the case of photo-refractive materials, the optical phase conjugation conversion efficiency thereof is generally about 1% or less, and for this reason, the actual application of the photo-refractive material is very limited due to a low signal-to-noise ratio and a small etendue caused by a narrow incident angle (R. W. Boyd, Nonliner Optics (Academic Press, 1992) Ch. 6). Usually, the phase conjugation conversion efficiency of the photo-refractive material can be increased using high-intensity input light. However, in ultrasound-modulated optical tomography for in vivo deep-tissue imaging, a low-intensity ultrasound-modulated optical signal is generated, and for this reason, the photo-refractive material has a limitation in that it cannot be applied to optical medical imaging.

In photoacoustic tomography (PAT), the detection of ultrasound that is generated based on the thermal expansion of bio-tissue by induction of light wave absorption is the core of optical imaging (Science Vol. 335, p. 1458 (2012)). To make photoacoustic tomography useful, light-absorbing substances, for example, erythrocytes, should be activated. In other words, photoacoustic tomography cannot be used for general purposes such as medical imaging diagnosis. Furthermore, to apply photoacoustic tomography to in vivo deep-tissue imaging, femtosecond high-power energy should be used, and the reason is to overcome scattering in tissue and to allow a sufficient amount of light to reach a desired point (Opt. Lett. Vol. 30, p. 507 (2005). Although cm-deep PAT optical imaging potentials have recently been reported in in vivo models (phantom tissues), photoacoustic tomography is generally applied to in vivo tissue as shallow as skin deep by use of hemoglobin or a fluorescent substance (Science Vol. 335, p. 1458 (2012)).

Ultraslow light is a typical nonlinear quantum optical phenomenon, the group velocity of light waves can be controlled by subjecting a resonant dispersive medium to non-absorption transmission by use of electromagnetically induced transmission (EIT: Physics Today Vol. 50, No. 7, p. (1997)) or spectral hole burning effect (Nature Communications Vol. 5, p. 3627 (2014); Opt. Exp. Vol. 17, p. 9369 (2009)). In 1999, Harris and his research team observed that the group velocity of light in a Bose-Einstein condensate was reduced up to 17 m/s (Nature Vol. 397, p. 594 (1999). In 2002, Ham and his research team observed that the group velocity of light in a $Pr^{3+}$-doped $Y_2SiO_5$ (Pr:YSO) solid medium was 30 m/s (Phys. Rev. Lett. Vol. 88, p. 023602 (2002). These two first observations of ultraslow light are based on EIT, and the EIT is a typical quantum interference effect which results from two-photon coherence in a three-level photorefractive medium that interacts with two resonant light pulses. Ham et al. also observed ultraslow light by the spectral hole burning method rather than the EIT, and the group velocity of the observed light was about 300 m/s (Opt. Exp. Vol. 17, p. 9369 (2009)). It is generally difficult to achieve EIT in solid media, because the Rabi frequency of light should be larger than the inhomogeneous broadening of the corresponding resonant frequency, and this condition is not achieved in almost all solid media by use of general commercial lasers. Ham et al. modified a Pr:YSO solid medium by spectral hole burning in 1997, which is the world's first modification, and observed EIT in 1997, and also observed and reported ultraslow light completely separated from signal light pulses, in 2002 (Opt. Communi. Vol. 144, p. 227 (1997); Phys. Rev. Lett. Vol. 88, p. 023602 (2002)).

A general phase conjugation phenomenon is obtained using light having the same wavelength in a two-level or four-level degenerate energy system. The physical principle in this general degenerate phase conjugation or degenerate four-wave mixing process is the density grid of light coherence-based medium. Thus, the phase conjugation linewidth is limited by the physical constant of the medium, that is, decay rate or dipole moment (oscillator strength). Herein, the phase conjugation conversion efficiency can be increased merely by increasing the intensity of light pumping. However, phase matching conditions in the medium result in narrowing of the angle variation of input signal light, thereby limiting the application of the light. Furthermore, in ultrasound-modulated optical tomography, the intensity of modulated light is very weak due to in vivo scattering, and thus the intensity of phase conjugation is also very low.

Meanwhile, a nondegenerate phase conjugation phenomenon is produced based on two-photon-induced spin coherence (i.e., moving coherence grating) in a three-level energy system that interacts with two difference light waves. Ham et al. observed nondegenerate four-wave mixing (Opt. Lett. Vol. 22, p. 1138 (1997)) in 1997 by use of a solid medium and also observed nondegenerate optical phase conjugation (Phys. Rev. A Vol. 59, p. R2583 (1999)), which are the world's first observations. Herein, the linewidth of the nondegenerate phase conjugation is determined by the spin phase shift time. Unlike degenerate phase conjugation, EIT-based nondegenerate phase conjugation is based on the fact that the intensity of input signal light is very weak, and this condition almost perfectly satisfies the limit condition of ultrasound-modulated optical tomography, that is, the weak ultrasound-modulated optical signal condition. The conversion efficiency of nondegenerate phase conjugation is limited by two-photon-induced spin phase coherence according to the EIT intensity. Very importantly, nondegenerate phase conjugation is amplified by the control of atomic density to a certain level and the control of the EIT intensity (Opt. Lett. Vol. 20, p. 982 (1995); Opt. Lett. Vol. 24, p. 86 (1999).

The most interesting phenomenon in nondegenerate optical phase conjugation is ultraslow light-enhanced conversion efficiency (Phys. Rev. A Vol. 68, p. 041801(R) (2003)). This is because temporal/spatial energy density is increased by ultraslow light, and this energy density is increased by slow constant h ($h=c/v_g$, $v_g$=group velocity of ultraslow light), and solid slow constant h observed by Ham et al. is $10^7$ (Phys. Rev. Lett. Vol. 88, p. 023602 (2002).

Ham et al. recently observed photon-echo as ultraslow light-amplified phase conjugation, and the size of the observed photo-echo was several thousand times greater than that of conventional photo-echo (OSA NLO 2015 conference, W4A, Hawaii, USA (2015)). In a rubidium vapor EIT system, Scully et al. observed slow light-enhanced nondegenerate phase conjugation (Phys. Rev. Lett. Vol. 82, p. 5229 (1999)). Harris et al. first identified and demonstrated slow light-enhanced nondegenerate four-wave mixing processes (Rev. Lett. Vol. 82, p. 4611 (1999)).

Photodynamic therapy is a method for treating diseases (including cancer) using light, and uses a photosensitizer or a photosensitizing agent. According to the principle of photodynamic therapy, when a photosensitizer is excited with light having a specific wavelength, the photosensitizer activates the surrounding oxygen so as to kill the surrounding cells (Nature Reviews Cancer Vol. 5, p. 380 (2003). Thus, slow light-amplified nondegenerate phase conjugate waves may be applied not only to optical imaging, but also to photodynamic therapy. Up to now, a real-time noninvasive photodynamic therapy method has not been reported.

SUMMARY

The present invention has been made in order to solve the above-described technical problems, and it is an object of the present invention to provide a method which can significantly increase the signal-to-noise ratio of an ultrasound-modulated optical signal by overcoming the shallow depth problem of in vivo optical imaging in existing optical imaging by use of a quantum optical phenomenon based on ultraslow light and nondegenerate phase conjugation and which can be applied directly not only to medical optical imaging, but also to medical photodynamic therapy, through slow light amplification of phase conjugate waves.

Another object of the present invention is to apply known ultrasound-modulated optical tomography to nonlinear quantum optics (ultraslow light) to thereby provide a high-resolution noninvasive optical imaging technology that automatically restores scattered and distorted optical images by ultraslow light-based nondegenerate conjugation, and also provide a photodynamic therapy technology that automatically focuses nondegenerate phase conjugate waves by targeting an in vivo deed-tissue ultrasound target region by a fluorescent substance.

To achieve the above objects, in accordance with an embodiment of the present invention, a noninvasive in vivo deep-tissue optical imaging apparatus based on ultraslow light and nondegenerate phase conjugation is disclosed.

The optical imaging apparatus may include: a light wave generating unit configured to transmit light to a target region; an ultrasound generating unit configured to transmit ultrasound to the target region; a light condensing unit configured to condense ultrasound-modulated light reflected from the target region; and a quantum processing unit configured to generate nondegenerate phase-conjugated light corresponding to the ultrasound-modulated light, wherein the nondegenerate phase-conjugated light may be transmitted from the light condensing unit to the target region to image the target region.

The quantum processing unit may include: an optical medium that generates the ultraslow light and the nondegenerate phase conjugation; first and second light pumping means configured to allow two pumping lights to be incident to the optical medium, respectively; and a light control unit configured to control the ultrasound-modulated light and the nondegenerate phase-conjugated light.

The optical medium may include at least four energy levels.

The light control unit may include an optical splitter configured to collect the nondegenerate phase-conjugated light.

The optical imaging apparatus may further include: a light wave modulating unit configured to perform at least one of modulation, frequency scan and condensation of light generated from the light wave generating unit; and an ultrasound modulating unit configured to perform at least one of modulation, frequency scan and three-dimensional space focusing of ultrasound generated from the ultrasound generating unit.

The optical imaging apparatus may further include an ultrasound/light wave sink unit configured to synchronize the light wave generating unit with the ultrasound generating unit.

The optical imaging apparatus may further include an optical switching unit configured to transmit light between the light condensing unit and the quantum processing unit by use of a free space or an optical fiber.

In accordance with another embodiment of the present invention, a noninvasive, in vivo deep-tissue photodynamic therapy apparatus based on ultraslow light and nondegenerate phase conjugation is disclosed.

The photodynamic therapy apparatus includes: a light wave generating unit configured to transmit light to a target region; an ultrasound generating unit configured to transmit ultrasound to the target region; a light condensing unit configured to condense ultrasound-modulated light reflected from the target region; and a quantum processing unit configured to generate nondegenerate phase-conjugated light corresponding to the ultrasound-modulated light, wherein the nondegenerate phase-conjugated light may be transmitted from the light condensing unit to the target region so as to be focused on a target substance present in the target region.

The quantum processing unit may include: an optical medium that generates the ultraslow light and the nondegenerate phase conjugation; first and second light pumping means configured to allow two pumping lights to be incident to the optical medium, respectively; and a light control unit configured to control the ultrasound-modulated light and the nondegenerate phase-conjugated light.

The optical medium may include at least four energy levels.

The photodynamic therapy apparatus may further include: a light wave modulating unit configured to perform at least one of modulation, frequency scan and condensation of light generated from the light wave generating unit; and an ultrasound modulating unit configured to perform at least one of modulation, frequency scan and three-dimensional space focusing of ultrasound generated from the ultrasound generating unit.

The photodynamic therapy apparatus may further include an ultrasound/light wave sink unit configured to synchronize the light wave generating unit with the ultrasound generating unit.

The photodynamic therapy apparatus may further include an optical switching unit configured to transmit light between the light condensing unit and the quantum processing unit by use of a free space or an optical fiber.

In accordance with still another embodiment of the present invention, a noninvasive, in vivo deep-tissue optical imaging method based on ultrasound light and nondegenerate phase conjugation is disclosed.

The method may include: a step of transmitting light to a target region; a step of transmitting ultrasound to the target region; a step of condensing ultrasound-modulated light reflected from the target region; and a quantum processing step of generating nondegenerate phase-conjugated light corresponding to the ultrasound-modulated light, wherein the nondegenerate phase-conjugated light may be transmitted from the light condensing unit to the target region to image the target region.

The quantum processing step may further include a step of allowing two pumping lights to be incident to an optical medium, thereby generating the nondegenerate phase-conjugated light from the ultrasound-modulated light.

The optical medium may include at least four energy levels.

The method may further include a step of collecting the nondegenerate phase-conjugated light to perform optical imaging.

The step of transmitting the light may include a light wave modulating step of performing at least one of modulation, frequency scan and condensation of the generated light, and the step of transmitting the ultrasound to the target region may include an ultrasound modulating step of performing at least one of modulation, frequency scan and three-dimensional space focusing of the generated ultrasound.

In accordance with still another embodiment of the present invention, a noninvasive, in vivo deep-tissue photodynamic therapy method based on ultrasound light and nondegenerate phase conjugation is disclosed.

The method may include: a step of transmitting light to a target region; a step of transmitting ultrasound to the target region; a step of condensing ultrasound-modulated light reflected from the target region; and a quantum processing step of generating nondegenerate phase-conjugated light corresponding to the ultrasound-modulated light, wherein the nondegenerate phase-conjugated light may be transmitted from the light condensing unit to the target region so as to be focused on a target substance present in the target region.

The quantum processing step may further include a step of allowing two pumping lights to be incident to an optical medium, thereby generating the nondegenerate phase-conjugated light from the ultrasound-modulated light.

The optical medium may include at least four energy levels.

The step of transmitting the light may include a light wave modulating step of performing at least one of modulation, frequency scan and condensation of the generated light, and the step of transmitting the ultrasound to the target region may include an ultrasound modulating step of performing at least one of modulation, frequency scan and three-dimensional space focusing of the generated ultrasound.

Figure 5:
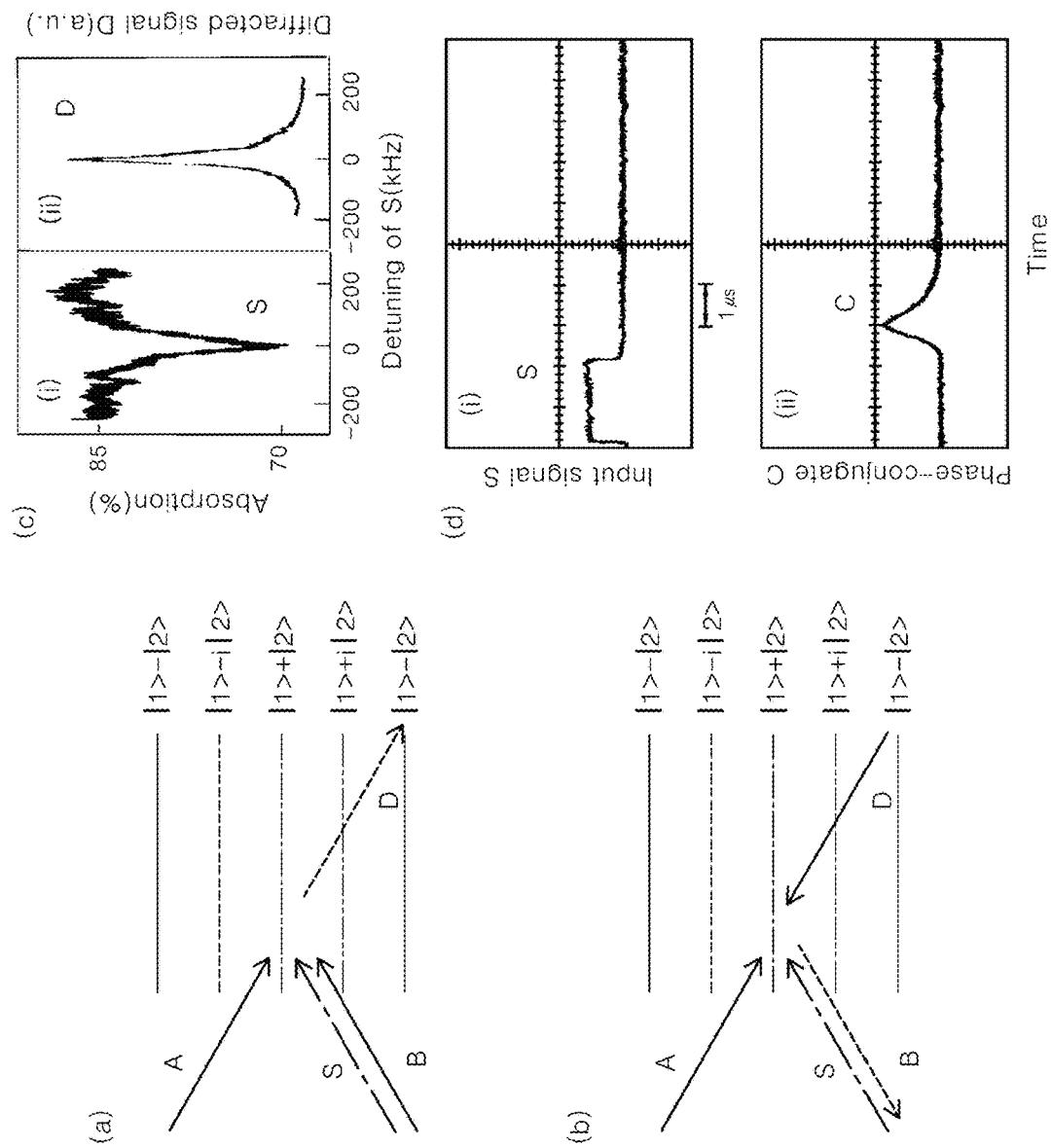

(a) of FIG. 5 and (b) of FIG. 5 show computer simulations indicating nondegenerate four-wave mixing process and nondegenerate phase conjugation, respectively, which satisfy phase match conditions according to an embodiment of the present invention.

(c) of FIG. 5 and (d) of FIG. 5 show experimental observations for (a) and (b) of FIG. 5, respectively, in the present invention.

Figure 2:
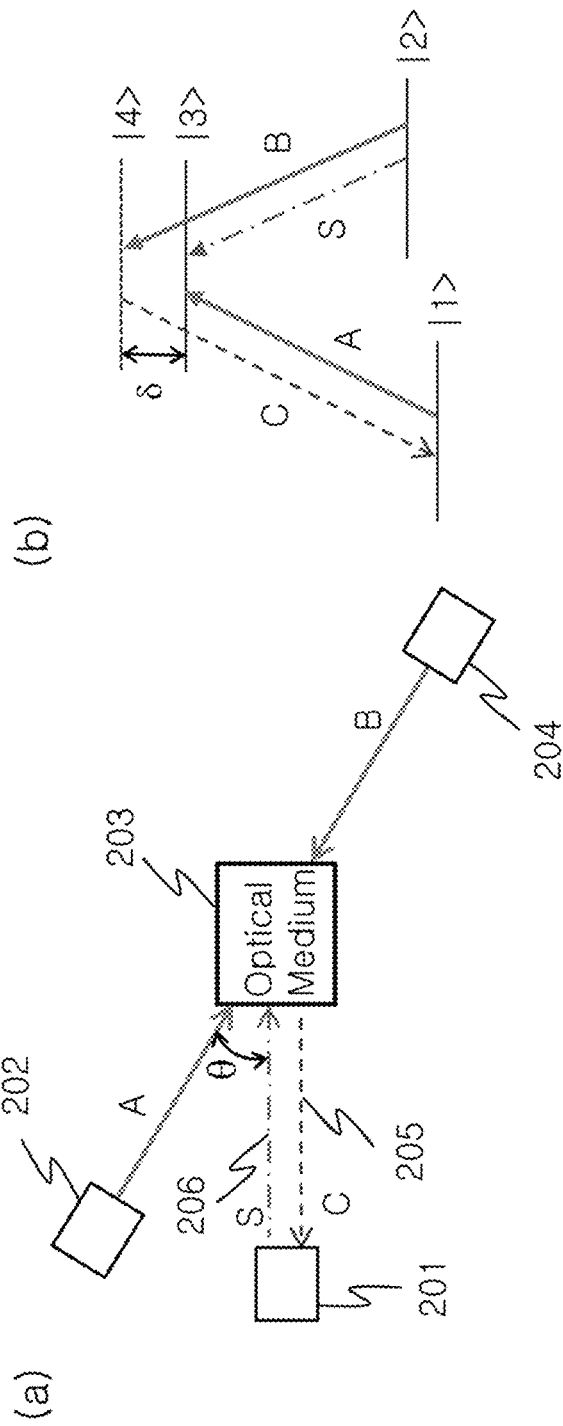
FIG. 2 shows the energy levels of an optical medium in the quantum processing unit of FIG. 1 according to an embodiment of the present invention and the configuration of input light and output light that act on the optical medium.
Figure 6:
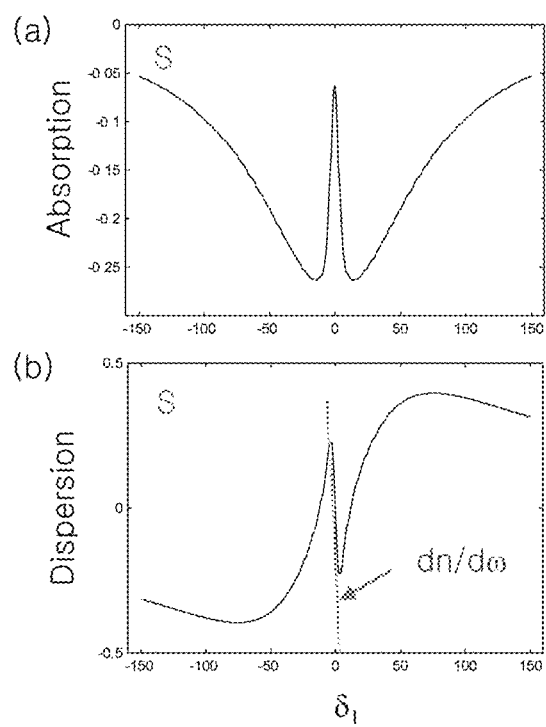
Figure 6:
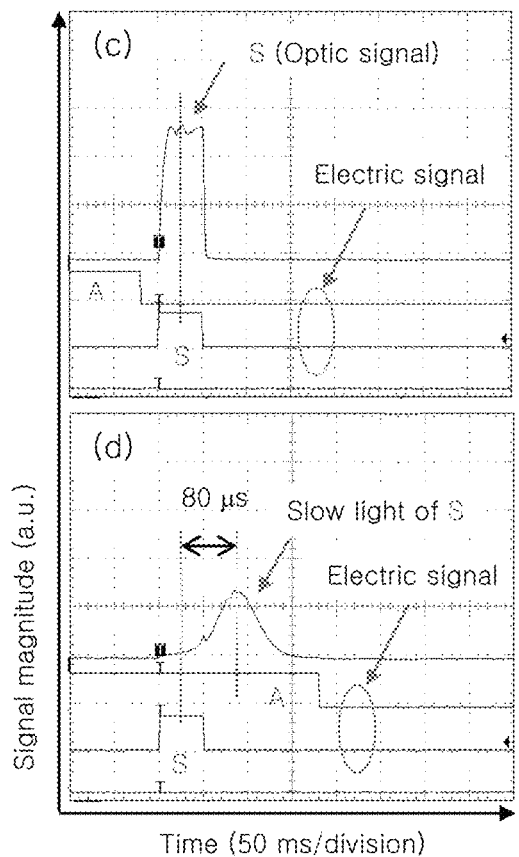

(a) of FIG. 6 and (b) of FIG. 6 show the results of light-medium interactions in FIG. 2 in the present invention, and computer simulations of electromagnetically induced transmission, which indicate the absorption and dispersion of light waves, respectively.

(c) of FIG. 6 and (d) of FIG. 6 show experimental results corresponding to one which became slower and one which did not become slower, respectively, for signal light S in (a) and (b) of FIG. 6 of the present invention.

Figure 7:
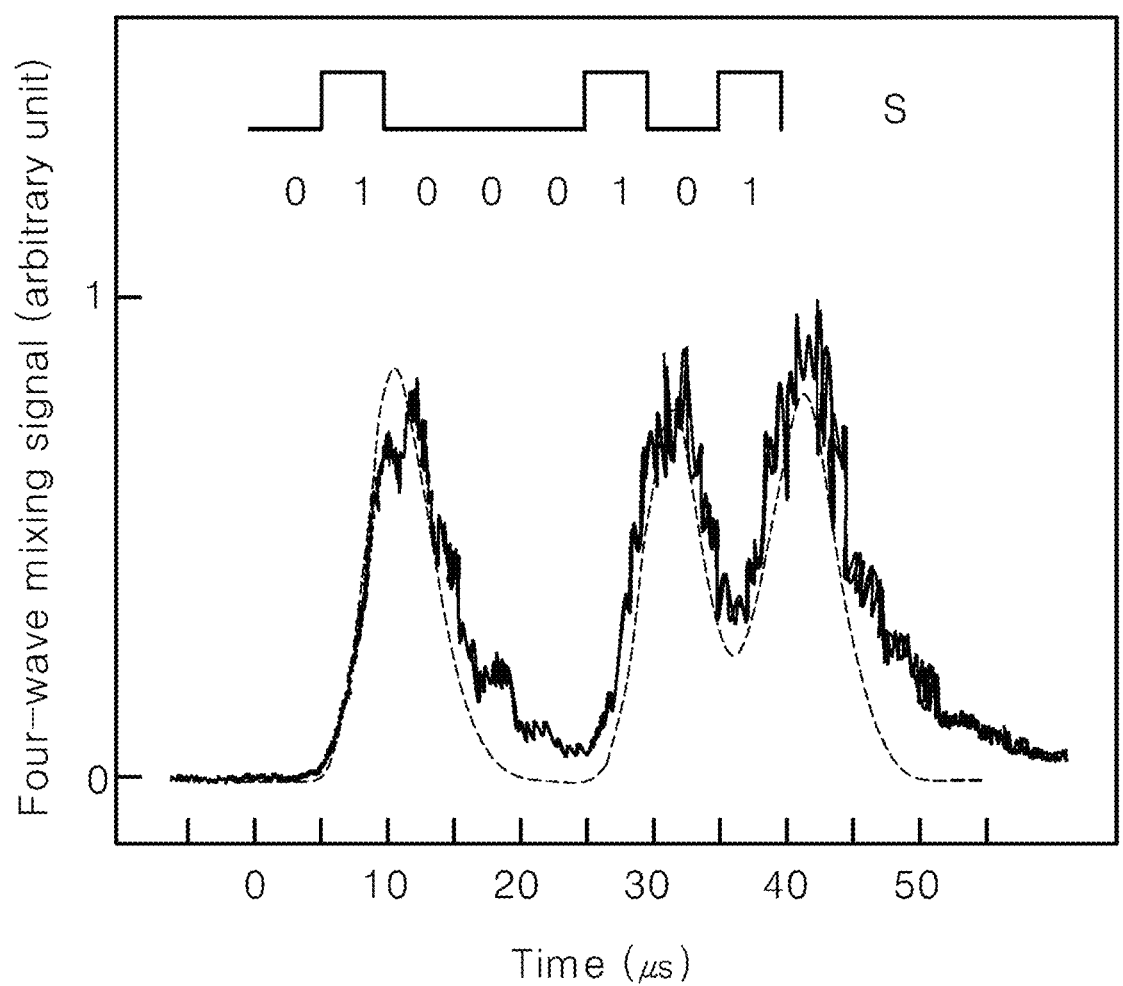

FIG. 7 shows a computer simulation (dotted line) and experimental observation for a nondegenerate four-wave mixing process much shorter than the optical density shift time by use of the continuous optical pulse signal light S in FIG. 2 of the present invention.

DETAILED DESCRIPTION

Hereinafter, ultraslow light and nondegenerate phase conjugation-based real-time, noninvasive, in vivo deep-tissue optical imaging and photodynamic therapy methods according to embodiments of the present invention will be described in detail with reference to the accompanying drawings.

It is to be understood that the following embodiments of the present invention are intended to embody the present invention and are not intended to restrict or limit the scope of the present invention. Contents that can be easily derived by those skilled in the art from the detailed description and embodiments of the present invention are interpreted as falling within the scope of the present invention.

Figure 1:
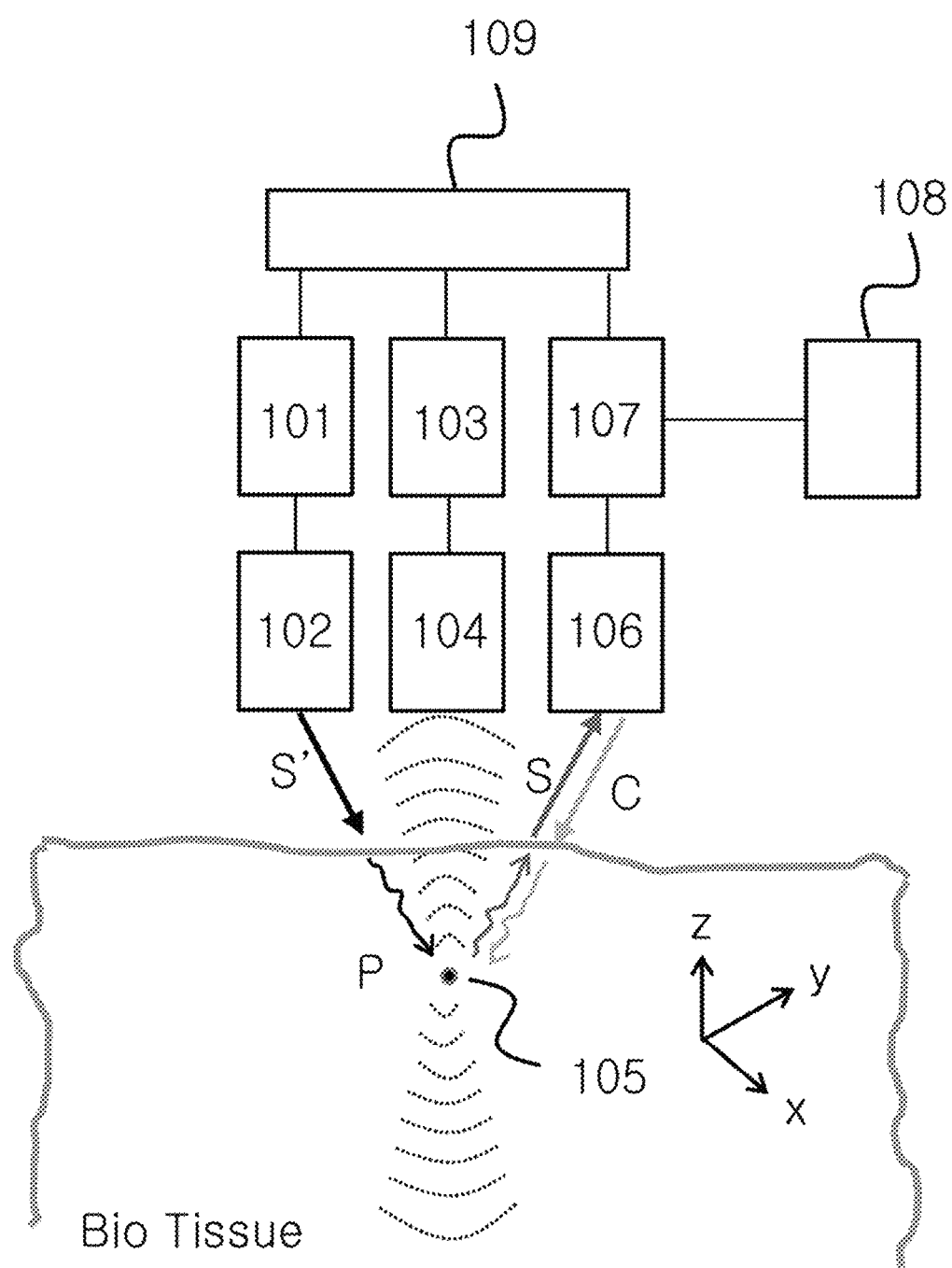
FIG. 1 shows the configuration of ultraslow light and nondegenerate phase conjugation-based real-time, noninvasive, in vivo deep-tissue optical imaging and photodynamic therapy methods according to embodiments of the present invention.

FIG. 1 shows the configuration of a system for ultraslow light and nondegenerate phase conjugation-based real-time, noninvasive, in vivo deep-tissue optical imaging and photodynamic therapy methods according to an embodiment of the present invention.

As shown in FIG. 1, a system according to an embodiment of the present invention includes: a light wave generating unit 101; a light wave modulating unit 102 for light wave modulation, frequency scan and light condensation; an ultrasound generating unit 103; an ultrasound modulating unit 104 for ultrasound modulation, frequency scan and three-dimensional space focusing; an ultrasound target region 105 capable of being targeted by a fluorescent substance; a light condensing unit 106 for ultrasound-modulated light waves and phase conjugate waves; a light switching unit 107 for light transmission from a free space or optical fiber; a quantum processing unit 108 configured to generate ultraslow light and quantum conjugation; and an ultrasound light waves sink unit 109. In FIG. 1, S' represents original light waves to be used for ultrasound modulation, and S represents ultrasound-modulated light waves. C represents phase conjugate waves produced from S by four-wave mixing process in the quantum processing unit. For photodynamic therapy, a fluorescent substance labeled with nanomaterial, dye or the like may target a target region, and phase conjugate waves amplified by ultralow light reverses the propagation direction of the ultrasound-modulated light waves S and are focused on the target substance to thereby achieve the treatment of diseases such as cancer cells.

The ultrasound generating unit 103 generates continuous waves, and the generated waves are pulsed, frequency-scanned and phase-modulated by the modulating unit 104, and focused on the target region 105 spatially located in the bio-tissue. The light waves S' generated from the light wave generating unit 101 are modulated to the waves S in the ultrasound target region and scattered.

(a) of FIG. 2 shows the detailed construction of the quantum processing unit 108 shown in FIG. 1. As shown therein, the quantum processing unit includes: an optical medium 203 that generates ultraslow light and nondegenerate phase conjugation; two pumping lights 202 and 204 that are incident to the optical medium; and a light control unit 201 configured to control ultrasound-modulated light waves 206 (S) and phase conjugate waves 205 (C). The light control unit 201 connects ultrasound-modulated light waves and phase conjugate waves to a free space or optical fiber.

(b) of FIG. 2 shows the energy levels of the optical medium 203 shown in (a) of FIG. 2 and light waves that act thereon. The optical medium has nonlinear optical characteristics and is composed of at least four energy levels $|1\rangle$, $|2\rangle$, $|3\rangle$ and $|4\rangle$. Among the four energy levels, $|1\rangle$ and $|2\rangle$ are in a ground state, and the energy level $|1\rangle$ is slightly lower than the energy level $|2\rangle$. In addition, $|3\rangle$ and $|4\rangle$ are in an excited state, and $|4\rangle$ is an actual or imaginary energy level which is higher or lower than the energy level $\beta\rangle$.

According to a phase match condition, the phase conjugate waves 205 are generated from three light waves 202, 204 and 206 acting on the optical medium 205, and are amplified by ultraslow light. For this, the pumping light 204 should act on ultraslow light of ultrasound-modulated light waves in a pulse form. The phase conjugate waves accurately reverse the propagation direction of the ultrasound-modulated light waves S in a time-reverse manner without phase changes.

Figure 3:
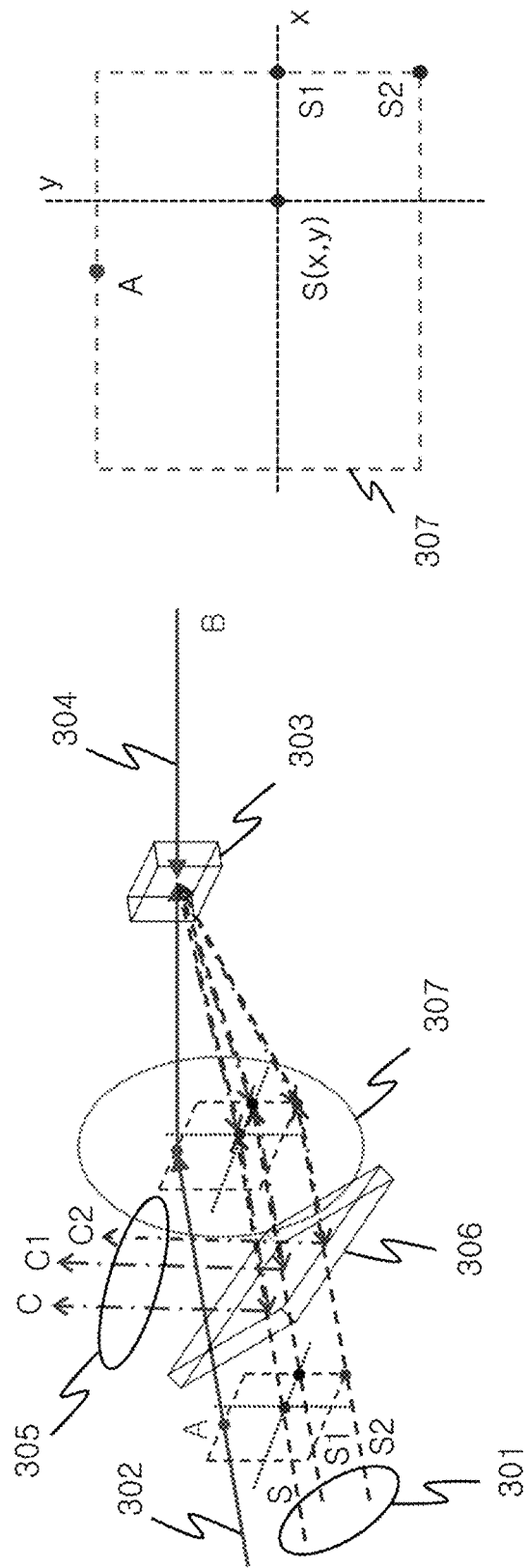
FIG. 3 shows the principles of optical imaging and photodynamic therapy, which satisfy high etendue by use of multiple optical signals in real-time, in vivo deep-tissue optical imaging and photodynamic therapy based on ultraslow light and nondegenerate phase conjugation according to embodiments of the present invention.

FIG. 3 shows the detailed configuration of the light control unit 201 shown in FIG. 2. The angle between the incident light S and the pumping light A changes variously depending on the nondegenerate phase conjugation of the present invention, and thus a plurality of S waves (e.g., S1, S2, S, etc.) which are incident at different angles, that is, two-dimensional information, are converted to a plurality of phase conjugate waves (C1, C2, C, etc.) and appear. In other words, three-dimensional images of the ultrasound target region can be restored to phase conjugate waves. Herein, for the purpose of optical imaging, the phase conjugate waves are collected by an optical splitter 306 and restored to images, and for the purpose of photodynamic therapy, the phase conjugate waves are not collected, or only a portion thereof is collected and the remaining portion proceeds as it is.

Figure 4:
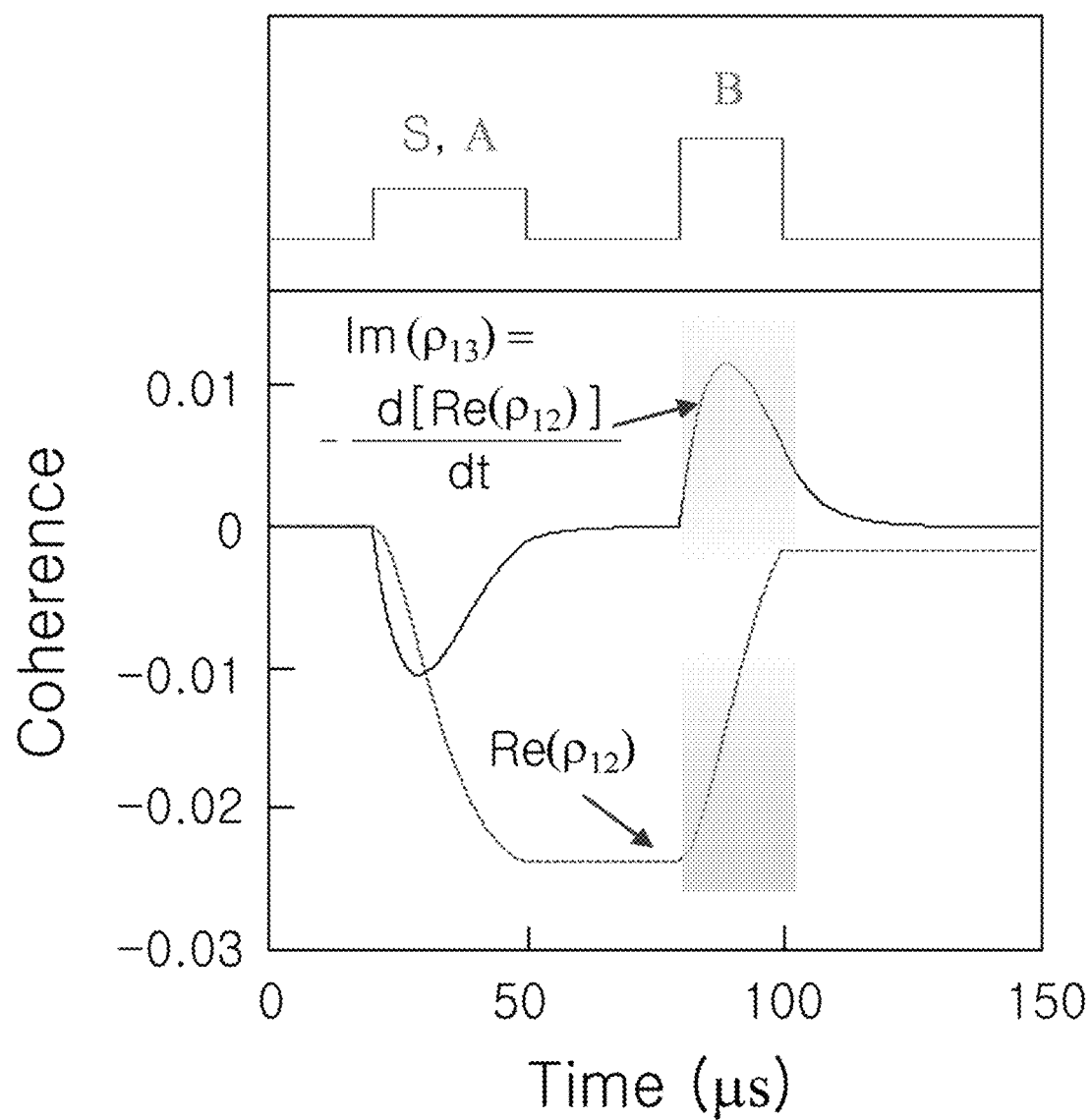
FIG. 4 shows a computer simulation of a typical nondegenerate four-wave mixing phenomenon, which indicates spin quantum coherence and quantum coherence-to-quantum coherence replacement for generation of two-photon-induced spin quantum coherence and generation of nondegenerate phase conjugation at spin energy levels based on electromagnetically induced transmission according to an embodiment of the present invention.

FIG. 4 shows computer simulation results calculated using a density function in order to indicate the quantum coherence and quantum coherence replacement produced by interaction of light waves that act on the optical medium of FIG. 2. First, two-photon spin quantum coherence (p12) is produced by the interaction between the pumping light A and the ultrasound-modulated light S, and when another pumping light B is applied thereto, phase conjugate wave ($\rho_{13}$) is quantum-mechanically generated: m($\rho_{13}$)=−d(Re ($\rho_{12}$))/dt. Herein, phase conjugate wave intensity (Id is proportional not only to two-photon spin quantum coherence intensity ($[Re(\rho_{12})]^2$), but also to pumping light intensity ($I_B$): $I_C \propto [Re(\rho_{12})]^{2\alpha} \cdot I_B$ (Opt. Exp. Vol. 16, p. 5350 (2008); Opt. Lett. Vol. 24, p. 86 (1999)).

(a) of FIG. 5 and (b) of FIG. 5 show the forward and backward of the nonlinear four-wave mixing process of FIG. 2, respectively, and (c) of FIG. 5 and (d) of FIG. 5 shows experimental results therefor (Opt. Lett. Vol. 22, p. 1138 (1997); Phys. Rev. A Vol. 59, p. R2583 (1999)). As shown in (c) of FIG. 5, the linewidth of four-wave mixing wave D follows the linewidth of electromagnetically induced transmission (EIT) of S, and the linewidth of EIT is only 10% of the linewidth of light wave used, explanation cannot be made only by a nonlinear optical phenomenon without a quantum offsetting phenomenon. As shown in (d) of FIG. 5, the temporal position of phase-conjugate C does not overlap the ultrasound-modulated light wave S, and this indicates the presence of two-photon quantum coherence lasting for the spin phase shift time (9 microseconds in Pr:YSO). Herein, the temporal position of the pumping light B follows the end of the pulses S and A.

(a) of FIG. 6 and (b) of FIG. 6 show computer simulation results for EIT occurring in the quantum medium of FIG. 2, and show the absorption spectrum and dispersion spectrum of the ultrasound-modulated optical signal S, respectively. Herein, the group velocity $v_g$ relies not only on the inherent refractive index n of the medium, but also on dn/dω related to dispersion. In EIT, the magnitude of dn/dω is much greater than that of n, and thus the very slow velocity of light is possible (Nature Vol. 397, p. 594 (1999)).

$$V_g = c \bigg/ \left(n + \omega \frac{dn}{d\omega}\right) \qquad \text{Equation 1}$$

This can be seen in the slow light of S experimentally observed in (d) of FIG. 6. Herein, η ($\eta = c/v_g$) indicating the degree of slow light is about $10^7$: medium length: 3 mm. (c) of FIG. 6 shows the absorption position of S alone without EIT and determines the standard of slow light.

Furthermore, in slow light, the spatial wavelength of the light is reduced by η, and thus the spatial energy density <E> is increased by η, thereby significantly increasing the nonlinear effect (Phys. Rev. Lett. Vol. 82, p. 4611 (1999)).

$$<E> \propto E \eta \qquad \text{Equation 2}$$

FIG. 7 shows a forward four-wave mixing signal generated by the continuous pulse of the ultrasound-modulated optical signal S. Generally, in nonlinear optics, the switching time of most optical devices, including wave mixing, is limited to the density shift time $T_1$ of medium. For this reason, the speed of an optical device comprising a semiconductor as a medium is usually less than 10 GHz. The medium used in FIG. 7 is Pr:YSO, and $T_1$ is 110 microseconds. The switching time shown in FIG. 7 is 10 microseconds, which is much shorter than $T_1$, and this time is the ground-state inter-energy (|1>−|2>) effective (or overall) spin phase shift time at which two-photon spin quantum coherence occurs. In other words, in the ultraslow light and nondegenerate phase conjugate-based real-time, noninvasive, in vivo deep-tissue optical imaging and photodynamic therapy methods of the present invention, the image reconstruction velocity is increased to an effective spin phase shift time much shorter than the limit of general optical media, indicating that the time required for optical tomography can be significantly reduced.

As described above, according to the ultraslow light and nondegenerate phase conjugation-based real-time, noninvasive, in vivo deep-tissue optical imaging and photodynamic therapy methods of the present invention, real-time in vivo deep-tissue optical imaging impossible in conventional optical imaging technology becomes possible, and photodynamic therapy also becomes possible. Thus, optical medical diagnosis and phototherapy technologies can be established in the future, and medical devices for non-radiation, noninvasive, real-time optical imaging/phototherapy can be realized.

In addition, the present invention will combine existing optical imaging with phototherapy, and thus provide a motivation to open the research field of Theranostics.

What is claimed is:

1. A noninvasive, in vivo deep-tissue optical imaging apparatus based on ultraslow light and nondegenerate phase conjugation, the apparatus comprising:
    a light wave generating unit configured to transmit light to a target region;
    an ultrasound generating unit configured to transmit ultrasound to the target region;
    a light condensing unit configured to condense ultrasound-modulated light reflected from the target region; and
    a quantum processing unit configured to generate nondegenerate phase-conjugated light corresponding to the ultrasound-modulated light, wherein the quantum processing unit comprises:
        an optical medium that generates the ultraslow light and the nondegenerate phase conjugation;
        first and second light pumping means configured to allow two pumping lights to be incident to the optical medium, respectively; and
        a light control unit configured to control the ultrasound-modulated light and the nondegenerate phase-conjugated light, wherein the light control unit comprises an optical splitter configured to collect the nondegenerate phase-conjugated light to image the target region.

2. The noninvasive, in vivo deep-tissue optical imaging apparatus of claim 1, wherein the optical medium comprises at least four energy levels.

3. The noninvasive, in vivo deep-tissue optical imaging apparatus of claim 1, further comprising:
   a light wave modulating unit configured to perform at least one of modulation, frequency scan and condensation of light generated from the light wave generating unit; and
   an ultrasound modulating unit configured to perform at least one of modulation, frequency scan and three-dimensional space focusing of ultrasound generated from the ultrasound generating unit.

4. The noninvasive, in vivo deep-tissue optical imaging apparatus of claim 1, further comprising an ultrasound/light wave sink unit configured to synchronize the light wave generating unit with the ultrasound generating unit.

5. The noninvasive, in vivo deep-tissue optical imaging apparatus of claim 1, further comprising an optical switching unit configured to transmit light between the light condensing unit and the quantum processing unit by use of a free space or an optical fiber.

6. A noninvasive, in vivo deep-tissue photodynamic therapy apparatus based on ultraslow light and nondegenerate phase conjugation, the apparatus comprising:
   a light wave generating unit configured to transmit light to a target region;
   an ultrasound generating unit configured to transmit ultrasound to the target region;
   a light condensing unit configured to condense ultrasound-modulated light reflected from the target region; and
   a quantum processing unit configured to generate nondegenerate phase-conjugated light corresponding to the ultrasound-modulated light,
   wherein the nondegenerate phase-conjugated light is transmitted from the light condensing unit to the target region so as to be focused on a target substance present in the target region, and
   wherein the quantum processing unit comprises:
      an optical medium that generates the ultraslow light and the nondegenerate phase conjugation;
      first and second light pumping means configured to allow two pumping lights to be incident to the optical medium, respectively; and
      a light control unit configured to control the ultrasound-modulated light and the nondegenerate phase-conjugated light.

7. The noninvasive, in vivo deep-tissue photodynamic therapy apparatus of claim 6, wherein the optical medium comprises at least four energy levels.

8. The noninvasive, in vivo deep-tissue photodynamic therapy apparatus of claim 6, further comprising:
   a light wave modulating unit configured to perform at least one of modulation, frequency scan and condensation of light generated from the light wave generating unit; and
   an ultrasound modulating unit configured to perform at least one of modulation, frequency scan and three-dimensional space focusing of ultrasound generated from the ultrasound generating unit.

9. The noninvasive, in vivo deep-tissue photodynamic therapy apparatus of claim 6, further comprising: an ultrasound/light wave sink unit configured to synchronize the light wave generating unit with the ultrasound generating unit.

10. The noninvasive, in vivo deep-tissue photodynamic therapy apparatus of claim 6, further comprising: an optical switching unit configured to transmit light between the light condensing unit and the quantum processing unit by use of a free space or an optical fiber.

* * * * *